United States Patent [19]

Barnes

[11] Patent Number: 4,929,291

[45] Date of Patent: May 29, 1990

[54] PROPELLANT CONTAINING 2-HYDROXYMETHYL-1,3-PROPANEDIOL TRINITRATE

[75] Inventor: Michael W. Barnes, Warrenton, Va

[73] Assignee: Thiokol Corporation, Ogden, Utah

[21] Appl. No.: 333,728

[22] Filed: Mar. 30, 1989

Related U.S. Application Data

[63] Continuation of Ser. No. 757,191, Jul. 22, 1985, abandoned, which is a continuation of Ser. No. 592,732, Mar. 22, 1984, abandoned, which is a continuation of Ser. No. 332,030, Dec. 15, 1981, abandoned, which is a continuation of Ser. No. 66,195, Aug. 13, 1979, abandoned, which is a continuation of Ser. No. 854,946, Nov. 25, 1977, abandoned.

[51] Int. Cl.$^5$ .............................................. C06B 45/10
[52] U.S. Cl. ..................................... 149/19.4; 149/88
[58] Field of Search ....................... 149/19.4, 19.8, 88; 558/484

[56] References Cited

U.S. PATENT DOCUMENTS

| | | | |
|---|---|---|---|
| 1,307,032 | 6/1919 | Barab | 149/88 |
| 2,066,506 | 1/1937 | Woodbury et al. | 44/72 |
| 2,545,538 | 3/1951 | Barnhart et al. | 260/467 |
| 2,709,130 | 5/1955 | Rinkenbach | 149/88 |
| 3,140,210 | 7/1964 | Sampson | 149/88 |
| 3,300,348 | 1/1967 | Griffith | 149/19.8 |
| 3,375,148 | 3/1968 | Finnegan et al. | 149/19.8 |
| 3,782,900 | 1/1974 | Dykes et al. | 23/230 R |
| 3,798,090 | 3/1974 | Allabashi | 149/19.8 |
| 4,091,040 | 5/1978 | Neilsen | 260/467 |
| 4,336,408 | 6/1982 | Barnes | 558/484 |
| 4,394,329 | 7/1983 | Barnes | 260/467 |

OTHER PUBLICATIONS

CPIA/M3, Unit 17, The Johns Hopkins University Applied Physics Lab., "TMETN", Aug. 1981, pp. 1–5.
CPIA/M3, Unit 37, The Johns Hopkins University Applied Physics Lab., "NG", Nov. 1983, pp. 1–14.
CPIA/M3, Unit 18, The Johns Hopkins University Applied Physics Lab., "BTTN", Aug. 1981, pp. 1–4.
Woodman, Alan L. and Adicoff, Arnold, "Vapor Pressure of Triacetin, Triethylene Glycol Dinitrate, and Metriol Trinitrate", J. Chem. Eng. Data, vol. 8, No. 2, Apr. 1963, pp. 241–242.
AMCP 706-177, Engineering Design Handbook, Explosive Series Properties of Explosives of Military Interest, U.S. Army Material Command, Mar. 1967, pp. 40, 206, and 233.
Meyer, "Explosives", Verlag Chemie, pp. 101, 102 & 181 (1977) New York.
Whittaker, Chem. Abs., 51, Abs. #13478(b), 1957.
Fujii, Rev. Phys. Chem. Japan, 20, 153-7 (1946).
Breusch et al, Chemische Berichte, 88, 1511–9 (1955).
Boros et al, J. Am. Chem. Soc., 88, 1140-3 (1966).

*Primary Examiner*—Edward A. Miller
*Attorney, Agent, or Firm*—Allen H. Erickson

[57] ABSTRACT

Propellant containing an oxidizer, a binder, and 2-hydroxymethyl-1,3-propanediol as a plasticizer.

1 Claim, No Drawings

PROPELLANT CONTAINING 2-HYDROXYMETHYL-1,3-PROPANEDIOL TRINITRATE

This is a continuation of co-pending application Ser. No. 757,191, filed on July 22, 1985, now abandoned, which is a continuation of co-pending application Ser. No. 592,732, filed on Mar. 22, 1984, now abandoned, which is a continuation of Ser. No. 332,030, filed Dec. 15, 1981, now abandoned, which is a continuation of Ser. No. 066,195, filed Aug. 13, 1979, now abandoned, which is a continuation of Ser. No. 854,946, filed Nov. 25, 1977, now abandoned.

BACKGROUND OF THE INVENTION

Crosslinked plasticized propellants are well-known as high energy propellants. These propellants employ nigtroglycerin as a plasticizer.

Nitroglycerin has a number of undesirable qualities which limits the usefulness of propellants employing it. The principal deficiencies are:

(1) Marginal thermal stability coupled with auto catalysis of the decomposition by the decomposition products requiring elaborate stabilization systems to provide adequate shelf life;

(2) Difficulty in achieving high solids loading;

(3) Difficulty in achieving good mechanical properties by using HMX coating agents; and (4) A relatively high vapor pressure causing exudation during vacuum processing, and migration over long periods at ambient temperatures and pressures.

The present invention relates to a novel compound 2-hydroxymethyl-1,3-propanediol trinitrate and its use in replacing nitroglycerin in plasticized propellants to ameliorate the problems associated with the use of nitroglycerin.

DISCUSSION OF THE PRIOR ART

The following references, copies of which accompany this application, are considered to have some relevance to the invention of this application.

Breusch and Oguzer in Chemische Berichte, Volumn 88, page 1511 (1955) reported a synthesis of 2-hydroxymethyl-1,3-propanediol (trimethylol methane) by lithium aluminum hydride reduction of methane tricarboxylic acid triethylester. They reported a 5% yield of a solid melting at 59°–62° C.

Boros et al in The Journal of the American Chemical Society, Volume 88, page 1140 (1966) reported a modification of the earlier synthesis of trimethylol methane. They reported an 18% yield of a low-melting solid.

Seiiti Fujii in Review of Physical Chemistry of Japan, Volume 20, page 153 (1946) discusses the products of hydrogenation of the condensation products of acetone and formaldehyde. He obtains one high melting product, which he names tetraglycerol, of melting point 178° C. and to which he assigns the structure $(HOCH_2)_3CH$. He also reports a trinitrate of this compound having a melting point of 137° C. The so-called tetraglycerol was identified by an "ultimate analysis" whose results are not reported. Based on the results later found by Breusch and Oguzer and by Boros et al as well as the data reported in this application which is consistent with their findings, whatever compound Fujii had, it was not trimethylol methane and hence he could not have prepared trimethylol methane trinitrate.

SUMMARY OF THE INVENTION

The tangible embodiment of the composition aspect of the invention possesses the inherent applied use characteristic of being a plasticizer for plasticized propellants.

The invention is a propellant composition comprising an oxidizer component, a binder component and 2-hydroxymethyl-1,3-propanediol trinitrate.

The tangible embodiments of this composition aspect of the invention possess the inherent applied use characteristics of being these propellants are more storage and processing stable than comparable propellants containing nitroglycerin in place of 2-hydroxymethyl-1,3-propanediol trinitrate.

DESCRIPTION OF THE PREFERRED EMBODIMENT

The preparation of the compositions of the invention may be performed by several processes.

2-Hydroxymethyl-1,3-propanediol trinitrate may be prepared by treating 2-hydroxymethyl-1,3-propanediol with excess nitric acid, conveniently anhydrous nitric acid, in the presence of a water absorber, conveniently fuming sulfuric acid, at below normal ambient temperature, conveniently 10°–15° C., conveniently in the presence of an immiscible solvent, conveniently methylene chloride, conveniently, but not essentially, while monitoring the redox potential of the system, while stirring. The immiscible solvent serves the convenient purpose of removing the nitrate ester from the acid phase as it is formed. Combination of reactants is conveniently accomplished by incremental addition of the alcohol to the acid. When the addition is complete, the reaction is essentially complete and the product may be removed by standard means. Separation of the phases, if the treatment has been performed in a 2 phase system, or the addition of a suitable immiscible solvent followed by separation of the organic phase permits recovery of 2-hydroxymethyl-1,3-propanediol trinitrate from the organic phase by standard techniques. If desired, recovery may be accomplished by neutralization of any acidity present in the organic phase, drying and evaporation of the solvent.

Propellant compositions may be prepared by using 2-hydroxymethyl-1,3-propanediol trinitrate in place of nitroglycerin in standard plasticized propellants.

The same standard processing techniques, as well as, standard propellant binders, oxidizers, and optionally the usual metal fuels, various adjuvants and cure and combustion catalysts and additional standard plasticizers may be employed as desired by the compounder.

2-Hydroxymethyl-1,3-propanediol may be prepared by a number of alternative procedures from known starting materials.

Bis-(hydroxymethyl) acetaldehyde may be treated in solution, conveniently aqueous solution, with hydrogen in the presence of a catalyst, conveniently at low to moderate pressures, 35 to 600 psi, preferably 50 to 500 psi using platinum, palladium or rhodium catalysts, preferably platinum, until a stoichiometric quantity of hydrogen is absorbed. Separation of the catalyst, followed by removal of the solvent is convenient method of recovering 2-hydroxymethyl-1,3-propanediol. It will be readily apparent to one skilled in the art that alternative means of reducing the aldehyde carbonyl group may be employed. An alkali metal, conveniently sodium, dissolving in a lower alkanol, conveniently ethanol (Bouveault Blanc reduction) is a convenient method.

Commercially available diethyl-bis(hydroxymethyl) malonate may be treated with a hydroxyl group protecting agent, conveniently acetone, in an inert water immiscible solvent, conveniently benzene, in the presence of an acid catalyst, conveniently phosphoric acid, at elevated temperature, conveniently the reflux temperature of the solvent employed, while separating the water which azeotropes with the solvent. If desired, when the theoretical quantity of water has been recovered the hydroxyl group protected product, in the case of acetone, 2,2-dimethyl-5,5-dicarbethoxy-1,3-dioxane, may be recovered by standard techniques. Separation and neutralization of the organic phase of the reaction mixture followed by evaporation of the inert solvent and any remaining hydroxyl group protecting agent is a convenient method. The hydroxyl protected product so produced may then be subjected to partial ester hydrolysis which will result in decarboxylation of the resultant $\beta$-carboxylic acid ester. Treatment in dimethyl sulfoxide in the presence of sodium chloride at elevated temperature, conveniently between 150° and 200° C., preferably between 170° and 180° C., with water while distilling water and ethanol is a convenient hydrolysis procedure. When the theoretical amount of ethanol has been recovered, the mixture may be cooled, partitioned between water and an immiscible solvent, conveniently ether, followed by separation and drying of the organic layer, evaporation of solvent and distillation of the hydroxyl protected, decarboxylated product, which if acetone is the protecting group will be 2,2-dimethyl-5-carbethoxy-1,3-dioxane.

This product may then be treated with an ester group reducing agent, conveniently lithium aluminum hydride, in a suitable solvent, conveniently ether, tetrahydrofuran or a mixture of ether and tetrahydrofuran, at ambient temperature. When the carboxyl function has been reduced the mixture may be decomposed with water, the solids removed by filtration and solvents evaporated to give the reduced hydroxyl protected product, which if acetone was the original protecting group will be 2,2-dimethyl-5-hydroxymethyl-1,3-dioxane. If desired the product may be purified by distillation in vacuo.

The protecting group may then be removed from the protected product by treatment with an appropriate hydrolytic system. If acetone was the original protecting group, treatment with aqueous hydrochloric acid at ambient temperature is a convenient method. The product, 2-hydroxymethyl-1,3-propanediol may be recovered by standard techniques. Evaporation of the hydrolysis mixture followed by recrystallization of the residual solid from acetone is a convenient method.

Tricarbo lower alkoxy methanes, available from di lower alkyl malonic esters by treatment with magnesium followed by lower alkyl chloroformates, may be treated with a borane-dimethyl sulfide adduct. After reduction of the carboxyl groups is complete, the reaction mixture may be decomposed with water, the resulting mixture partitioned between ether and water, the organic phase dried and solvent evaporated and the residue distilled to give 2-hydroxymethyl-1,3-propanediol.

The starting materials for the practice of the invention namely bis-(hydroxymethyl) acetaldehyde, di lower alkyl bis-(hydroxymethyl) malonate and tricarbo lower alkoxy methane are all commercially available or readily preparable by standard synthetic methods well-known in the literature. The preparation of bis-(hydroxymethyl) acetaldehyde is described by Vik in Acta Chimica Scandinavica, Vol. 27, page 239 (1973). Diethyl bis-(hydroxymethyl) malonate may be synthesized by a procedure described in Org. Synth. Vol. 40, page 27. The preparation of other lower alkyl esters by analogous methods will be obvious to one of average skill in the art. The general procedure for the synthesis of tricarbo lower alkoxy methanes has been outlined hereinabove. The borane-dimethyl sulfide adduct is commercially available.

One skilled in the art will recognize that in addition to acetone illustrated as a hydroxy group protecting agent for the hydroxyl groups on di ethyl-bis(hydroxymethyl) malonate many other standard hydroxyl protecting groups may be employed in that synthetic scheme. Among these are dihydropyran for the formation of tetrahydropyanyl ethers, and tri-lower alkyl silyl halides for the formation of tri-lower alkyl silyl esters.

Similarly the partial hydrolysis of the hydroxyl protected malonic diester to produce the decarboxylated half ester may be accomplished by any known ester hydrolysis reagent. One skilled in the art will, of course, adjust the conditions according to the hydroxyl protecting group.

Similarly the reduction of the remaining ester group to an alcohol may be accomplished by many methods equivalent to the use of lithium aluminum hydride as illustrated. Some known equivalents are the use of hydrogen adsorbed on known catalysts, borohydride reducing agents, other derivatives of $AlH_3$ and its complex salts, the borane-dimethyl sulfide adduct employed in the reduction of methane tricarboxylate esters, and Bouveault Blanc type reductions employing an alkali metal dissolving in a lower alkanol.

The requisite removal of the aforementioned hydroxyl group protecting agents may also be accomplished by known methods, for example, acid hydrolysis is suitable for the removal of tetrahydropyranyl ethers, while basic hydrolysis is preferable for tri-lower alkyl silyl ethers.

As used herein and in the appended claims the term "lower alkyl" comprehends a saturated hydrocarbon radical, either straight, branched chain or cyclic having from 1 to 8 carbon atoms. The term "lower alkanol" comprehends a monohydroxyl substituted lower alkyl group. The term "lower alkoxy" comprehends a radical derived from a lower alkanol by removal of the hydroxyl hydrogen.

The following Examples further illustrate the best mode contemplated by the inventor for the practice of his invention.

EXAMPLE 1

2-Hydroxymethyl-1,3-Propanediol from Bis-(hydroxymethyl) Acetaldehyde

To bis-(hydroxymethyl) acetaldehyde (from hydrolysis of its diethyl acetal (23 g) in water (300 ml.) is added $PtO_2$ (0.3 g) and $FeSO_4.7H_2O$ (0.02 g). This mixture is shaken with hydrogen at ambient temperature at 50 to 500 psi until the theoretical quantity (0.13 mole) of hydrogen is absorbed. The catalyst is then removed by filtration, the water removed to give a residue. Distillation of the residue gives 2-hydroxymethyl-1,3-propanediol (10.2 g) (74.5%) B.P. 140° C. (0.005 mm), M.P. 60°–62°.

EXAMPLE 2

2,2-Dimethyl-5,5-Dicarbethoxy-1,3-Dioxane

To diethyl-bis-(hydroxymethyl) malonate (50 g) in acetone (50 ml) and benzene (200 ml) is added phosphoric acid (10 g). The mixture is refluxed while stirring and separating water which distills. When water evolution is complete, the reaction mixture is cooled and the organic layer is separated, stirred with solid sodium carbonate (10 g), filtered and evaporated to give the title product (52 g) (87%) $n_D^{26}$ 1.4412.

EXAMPLE 3

2,2-Dimethyl-5-Carbethoxy-1,3-Dioxane

To a solution of the product of Example 2 (65 g) in dimethyl sulfoxide (65 g) is added sodium chloride (1 g). The mixture is stirred while warming at about 180° C., and water is added in small portions while maintaining the temperature between 170° and 180°. Ethanol and water are evolved and are removed by distillation until about 60 ml of liquid has been collected. The mixture is cooled, ether (200 ml) added, and the mixture partitioned with 3 portions of water (50 ml). The organic phase is dried over sodium sulfate and evaporated to a residue. Distillation of the residue gives the title product (25 g) (57%) B.P. 38° (0.01 mm) $n_D^{26}$ 1.4400.

EXAMPLE 4

2,2-Dimethyl-5-Hydroxymethyl-1,3-Dioxane

Lithium aluminum hydride (80 g) is stirred in ether (2000 ml) while the product of Example 3 (230 g) in ether (250 ml) is added dropwise. When the addition is complete the mixture is stirred an additional 16 hours. The reaction mixture is decomposed by careful addition of water (80 ml) followed by 15% aqueous sodium hydroxide (80 ml) and additional water (240 ml). The resulting suspension is filtered, the filter cake washed with ethanol and ether and the combined filtrates evaporated to give a residue. Distillation of the residue gives the title product (155 g) (81%) B.P. 75° C. (0.05 mm).

EXAMPLE 5

2-Hydroxymethyl-1,3-Propanediol

The product of Example 4 (14.6 g) is stirred in water (4 ml) containing concentrated hydrochloric acid (1 drop) for about 18 hours. Evaporation of the water gives a solid residue which is recrystallized from acetone to give the title product (9 g) (85%) M.P. 61°–62°.

EXAMPLE 6

2-Hydroxymethyl-1,3-Propanediol From Tricarboethoxy Methane

Tricarboethoxy methane (1 g) in hexane (or dry tetrahydrofuran) (5 ml) is treated with borane-dimethyl sulfide (2 ml). The reaction mixture is stirred 48 hours at 60° C. Methanol (50 ml) is then added dropwise slowly, avoiding excessive gassing. The volatile solvents are removed in vacuo to give a product (0.45 g) (m.p. 56°–60° C.), which after recrystallization from acetone affords the title product (m.p. 62°–63° C.).

EXAMPLE 7

2-Hydroxymethyl-1,3-Propanediol Trinitrate

To a mixture of methylene chloride (150 ml) and a 1:1 mixture of anhydrous nitric acid and 30% fuming sulfuric acid (40 ml) carefully stirred at 10° to 15% C. is added portionwise 2-hydroxymethyl-1,3-propanediol (7.5 g) while measuring the redox potential of the solution and maintaining it between −0.07 and 0.20 volts. This is conveniently done with an Ingold Redox probe charged with the mixed acid. When the addition is complete the phases are separated, the organic phase washed with water, aqueous sodium bicarbonate and aqueous urea, dried over sodium sulfate and/or molecular sieves and the solvent evaported to give the title product (15 g) m.p. 11°–12° C.,D 1.53, $n_D^{29.5}$ 1.4746.

Analysis for $C_4H_7N_3O_9$; Calculated: N 17.43%. Found: N 17.42%.

I. R. Analysis: $\lambda_{max}^{film}$: 2970, 1640, 1280, 860 cm$^{-1}$.

N. M. R. Analysis: Signals at: $\delta$=4.56 (doublet, 6H, —CH$_2$—ONO$_2$), 2.70 (heptet, 1H,

ppm.

EXAMPLE 8

The volatilities of nitroglycerin (NG), 2-hydroxymethyl-1,3-propanediol trinitrate (TMMTN), and 2,2-di(hydroxymethyl)-1-propanol trinitrate (TMETN) were measured at $5 \times 10^{-5}$ mm Hg and ambient temperature by determining weight decrease of samples of each material. Using the weight loss of nitroglycerin as a standard the results are

|  | Relative Weight Loss |
| --- | --- |
| NG | 1.0 |
| TMETN | 0.26 |
| TMMTN | 0.16 |

EXAMPLE 9

Thermal stabilities of nitroglycerin (NG) 2-hydroxymethyl-1,3-propanediol trinitrate (TMMTN) and 2,2-di-(hydroxymethyl)-1-propanol trinitrate (TMETN) were evaluated by a number of independent methods.

A. NG, TMMTN and TMETN were incorporated into standard KBr infra red pellets and the rate of disappearance of the nitrate ester peaks at 1640, 1280 and 840 cm$^{-1}$ determined at 100° and 140° C. the absolute and relative rate constants for the decomposition are as follows:

| FIRST ORDER RATE CONSTANT (R) × 10$^6$ (sec.$^{-1}$) | | | | | |
| --- | --- | --- | --- | --- | --- |
| Temp. °C. | Nitrate Ester | Average | 1640 cm$^{-1}$ | 1280 cm$^{-1}$ | 840 cm$^{-1}$ |
| 100 | TMMTN | 0.15 | 0.17 | 0.19 | 0.09 |
| 100 | NG | 0.29 | 0.37 | 0.30 | 0.22 |
| 140 | TMMTN | 2.24 | 2.82 | 2.65 | 1.26 |
| 140 | TMETN | 1.63 | 2.01 | 1.76 | 1.11 |
| 140 | NG | 3.90 | 4.70 | 3.85 | 3.16 |
| RELATIVE RATES | | | | | |
| Nitrate Ester | | 100° | | 140° | |
| NG | | 1.00 | | 1.00 | |
| TMMTN | | 0.52 | | 0.57 | |
| TMETN | | — | | 0.42 | |

B. NG, TMMTN and TMETN were sujected to differntial scanning calorimetry with the following results.

| Compound | Beginning of Exotherm (°C.) | Peak of Exotherm (°C.) |
|---|---|---|
| TMMTN | 175 | 212 |
| TMETN | 163 | 210 |
| NG | 168 | 193 |

C. The thermal stabilities as measured by gas evolution of NG, TMMTN and TMETN were measure at 90° C. with following results:

| Compound | Stability (ml/g/hr.) |
|---|---|
| TMMTN | 0.013 |
| TMETN | 0.020 |
| NG | 0.024 |

D. Samples of NG, TMMTN and TMETN were sealed in a closed pressure vessel for 23 hours at 93° C. with the following results.

| Compound | Pressure Generated |
|---|---|
| TMMTN | 0 |
| TMETN | 0 |
| NG | 107.8 mm Hg |

EXAMPLE 10

A propellant having the ingredients in the proportions shown is prepared.

| | Quantity (%) |
|---|---|
| 2-hydroxymethyl-1,3-propanediol trinitrate | 19.989 |
| PCP-260 (hydroxy terminated polycarprolactone, Union Carbide) | 4.872 |
| Desmodur N-100 (Polyfunctional isocyanate based on hexamethylene diisocyanate, Mobay) | 0.839 |
| 4-nitrodiphenylamine | 0.25 |
| Carbon Black | 1.0 |
| Triphenylbismuth | 0.05 |
| HMX (cyclotetramethylene tetranitramine) | 23.0 |
| Ammonium Perchlorate (90μ) | 20.0 |
| Ammonium Nitrate (200μ) | 30.00 |

The formulation shows less plasticizer bleeding than a comparable nitroglycerin formulation and enhanced storage stability while exhibiting only a slightly lowered specific impulse.

EXAMPLE 11

To further illustrate the relative performance of 2,2-di(hydroxymethyl)-1-propanol trinitrate (TMETN) nitroglycerin (NG) and 2-hydroxymethyl-1,3-propanediol trinitrate (TMMTN) plasticized propellants, computer simulations (which are known to have good correlation with actual performance) for the various propellant compositions shown below have been calculated to determine the specific impulse Isp and density ($\sigma$) to be expected of such compositions.

| Propellant 76% Solids, 58% Oxidizer (Ammonium perchlorate (AP) + HMX), 18% Al, Plasticizer/Polymer = 4.0/1 | | | | |
|---|---|---|---|---|
| Plasticizer | % AP | 0 | 5 | 10 |
| TMMTN | Isp (sec) | 272.1 | 272.1 | 271.4 |
| | $\sigma$(lb/in$^3$) | 0.0667 | 0.0668 | 0.0669 |
| NG | Isp (sec) | 272.9 | 272.2 | 271.4 |
| | $\sigma$(lb/in$^3$) | 0.0674 | 0.0675 | 0.0675 |

| Propellant 82% Solids, 64% Oxidizer (AP + HMX) remainder as above | | | | |
|---|---|---|---|---|
| Plasticizer | % AP | 0 | 5 | 10 |
| TMMTN | Isp (sec) | 273.9 | 273.3 | 272.6 |
| | $\sigma$(lb/in$^3$) | 0.0682 | 0.0683 | 0.0684 |
| NG | Isp (sec) | 274.2 | 273.4 | 272.2 |
| | $\sigma$(lb/in$^3$) | 0.0687 | 0.0688 | 0.0689 |

| Propellant 78% HMX, PCP/HDI Binder | | | | |
|---|---|---|---|---|
| Plasticizer/Polymer | | 3.5/1 | 4.0/1 | 4.5/1 |
| TMMTN | Isp (sec) | 254.9 | 256.0 | 256.8 |
| | $\sigma$(lb/in$^3$) | 0.0636 | 0.0637 | 0.0658 |
| NG | Isp (sec) | 257.9 | 259.0 | 259.9 |
| | $\sigma$(lb/in$^3$) | 0.0644 | 0.0646 | 0.0647 |
| TMETN | Isp (sec) | 252.1 | 253.2 | 254.0 |
| | $\sigma$(lb/in$^3$) | 0.0635 | 0.0636 | 0.0637 |

| Propellant 82% HMX, PCP/HDI Binder | | | | |
|---|---|---|---|---|
| Plasticizer/Polymer | | 3.5/1 | 4.0/1 | 4.5/1 |
| TMMTN | Isp (sec) | 256.9 | 257.7 | 258.4 |
| | $\sigma$(lb/in$^3$) | 0.0645 | 0.0646 | 0.0646 |
| NG | Isp (sec) | 259.3 | 260.2 | 260.9 |
| | $\sigma$(lb/in$^3$) | 0.0651 | 0.0653 | 0.0654 |
| TMETN | Isp (sec) | 254.7 | 255.5 | 256.2 |
| | $\sigma$(lb/in$^3$) | 0.0644 | 0.0645 | 0.0646 |

The subject matter which Applicant regards as his invention is particularly pointed out and distinctly claimed as follows.

1. A propellant composition consisting of:
   A. about 19.989% by weight trimethylolmethane trinitrate;
   B. about 4.872% by weight hydroxy-terminated polycaprolactone;
   C. about 0.839% by weight of a polyfunctional isocyanate based on hexamethylene diisocyanate;
   D. about 0.25% by weight 4-nitrodiphenylamine;
   E. about 1.0% by weight carbon black;
   F. about 0.05% by weight triphenylbismuth;
   G. about 23.00% by weight cyclotetramethylene tetranitramine;
   H. about 20.00% by weight ammonium perchlorate; and
   I. about 30.00% by weight ammonium nitrate.

* * * * *